US011744883B2

(12) United States Patent
Montane Giralt et al.

(10) Patent No.: US 11,744,883 B2
(45) Date of Patent: Sep. 5, 2023

(54) INTRADERMAL COMBINATION VACCINE AGAINST MYCOPLASMA AND PORCINE CIRCOVIRUS

(71) Applicant: HIPRA SCIENTIFIC, S.L.U., Girona (ES)

(72) Inventors: Jordi Montane Giralt, Sant Feliu de Pallerols (ES); Ester Puigvert Molas, Les Preses (ES); Alexandra Moros Sanz, Olot (ES); Marta Sitjà Arnau, Girona (ES)

(73) Assignee: HIPRA SCIENTIFIC, S.L.U., Amer (ES)

( * ) Notice: Subject to any disclaimer, the term of this patent is extended or adjusted under 35 U.S.C. 154(b) by 0 days.

(21) Appl. No.: 16/955,015

(22) PCT Filed: Dec. 19, 2018

(86) PCT No.: PCT/EP2018/085844
§ 371 (c)(1),
(2) Date: Jun. 17, 2020

(87) PCT Pub. No.: WO2019/121916
PCT Pub. Date: Jun. 27, 2019

(65) Prior Publication Data
US 2020/0376106 A1 Dec. 3, 2020

(30) Foreign Application Priority Data
Dec. 22, 2017 (EP) ..................................... 17382893

(51) Int. Cl.
*A61K 39/02* (2006.01)
*A61K 39/12* (2006.01)
(Continued)

(52) U.S. Cl.
CPC ........ *A61K 39/0241* (2013.01); *A61K 9/0019* (2013.01); *A61K 39/12* (2013.01);
(Continued)

(58) Field of Classification Search
None
See application file for complete search history.

(56) References Cited

U.S. PATENT DOCUMENTS 5,565,205 A * 10/1996 Petersen ................. A61P 31/04
424/264.1
9,120,859 B2 * 9/2015 Galvin .................... A61P 37/04
(Continued)

FOREIGN PATENT DOCUMENTS

WO  WO 2009/126356 A2  10/2009
WO  WO 2013/152086 A1  10/2013
(Continued)

OTHER PUBLICATIONS

Reddy et al. (Advanced Drug Delivery Reviews. 2009; 61: 1412-1426).*
(Continued)

*Primary Examiner* — Shanon A. Foley
(74) *Attorney, Agent, or Firm* — Saul Ewing LLP; Kathryn Doyle (57) ABSTRACT

The present invention provides a combination vaccine comprising one or more antigens of *Mycoplasma hyopneumoniae*, one or more antigens of Porcine circovirus, and pharmaceutically acceptable excipients and/or carriers, for use in the prevention and/or treatment of porcine enzootic pneumonia and/or Porcine Circovirus-Associated Diseases (PCVAD) by administration of the vaccine into the dermis of livestock, wherein the one or more antigens of porcine circovirus comprises the PCV2 ORF2 protein in an amount from 0.1 µg/dose to 10 µg/dose.

17 Claims, 3 Drawing Sheets

(51) Int. Cl.
*A61P 31/20* (2006.01)
*A61K 9/00* (2006.01)
*A61K 39/39* (2006.01)
*A61K 39/00* (2006.01)

(52) U.S. Cl.
CPC .............. *A61K 39/39* (2013.01); *A61P 31/20* (2018.01); *A61K 2039/521* (2013.01); *A61K 2039/54* (2013.01); *A61K 2039/545* (2013.01); *A61K 2039/552* (2013.01); *A61K 2039/55566* (2013.01); *A61K 2039/70* (2013.01)

(56) References Cited

U.S. PATENT DOCUMENTS

2009/0092636 A1* 4/2009 Roof .................. A61P 31/22
424/201.1
2020/0376106 A1* 12/2020 Montane Giralt ... A61K 9/0019

FOREIGN PATENT DOCUMENTS

| WO | WO 2014/009586 A2 | 1/2014 |
| WO | WO 2014/079943 A1 | 5/2014 |
| WO | WO 2014/182872 A1 | 11/2014 |
| WO | WO 2016/102619 A1 | 6/2016 |
| WO | WO 2017/116698 A1 | 7/2017 |
| WO | WO 2017/162741 A1 | 9/2017 |

OTHER PUBLICATIONS

Singh-Joy et al. (International journal of toxicology. 2008; 27: 93-128).*

International Search Report and Written Opinion dated Feb. 15, 2019 for PCT Application No. PCT/EP2018/085844, 14 pages.

Anonymous, "One-Dose Vaccination Against Mycoplasma hyopneumoniae and Porcine Circovirus Type 2", The Pig Site; MSD Animal Health; XP002781041, 4 pages; URL: HTTP:/thepigsite. com/articles/3191/onedose-vaccination-against-mycoplasma-hyopneumoniae-and-porcine-circovirus-type-2/ [retrieved Jul. 27, 2010], the whole document.

Boehringer Ingelheim, "Ingelvac® CircoFLEX-MycoFLEX (TM) Material Safety Data Sheet", Jun. 23, 2008, URL: http://www.bi-vetmedica.com/content/dam/internet/ah/vetmedica/com_EN/MSDS/Ingelvac_CircoFlex-MycoFlex_msds.pdf [retrieved Sep. 28, 2016] the whole document.

Caron, et al., "Diagnosis and differentiation of *Mycoplasma hyopneumoniae* and *Mycoplasma hyorhinis* infections in pigs by PCR amplification of the p36 and p46 genes", Journal of Clinical Microbiology Apr. 2000; vol. 38, No. 4, pp. 1390-1396.

Minion, et al., "The genome sequence of *Mycoplasma hyopneumoniae* strain 232, the agent of swine mycoplasmosis", Journal of Bacteriology Nov. 2004; vol. 186, No. 21, pp. 7123-7133.

Palinski, et al., "A Novel Porcine Circovirus Distantly Related to Known Circoviruses is Associated with Porcine Dermatitis and Nephropathy Syndrome and Reproductive Failure", Oct. 26, 2016; vol. 91, No. 1, 42 pages.

Pepovich, et al., "Clinical Testing of Combined Vaccine against enzootic pneumonia in industrial pig farming in Bulgaria", Macedonian Veterinary Review Jan. 1, 2015; vol. 38, No. 2, pp. 195-201; XP055474403; DOI: 10.14432.

Segales, et al., "PCV-2 genotype definition and nomenclature", The Veterinary Record, Letters, Jun. 28, 2008, vol. 162, No. 26, pp. 867-868.

Vasconcelos, et al., "Swine and poultry pathogens: the complete genome sequences of two strains of *Mycoplasma hyopneumoniae* and a strain of *Mycoplasma synoviae*", Journal of Bacteriology, Aug. 2005, vol. 187, No. 16, pp. 5568-5577.

Xiao, et al., "Global molecular genetic analysis of porcine circovirus type 2 (PCV2) sequences confirms the presence of four main PCV2 genotypes and reveals a rapid increase of PCV2d", Journal of General Virology, Feb. 23, 2015; vol. 96, Part 7, pp. 1830-1841.

* cited by examiner

INTRADERMAL COMBINATION VACCINE AGAINST MYCOPLASMA AND PORCINE CIRCOVIRUS

This application is a National Stage Application of International Application No. PCT/EP2018/085844 filed 19 Dec. 2018 which claims the benefit of European Patent application EP 1 738 2893.0, filed on Dec. 22, 2017. EP application 17382893.0 is incorporated herein by reference in its entirety and for all purposes.

TECHNICAL FIELD

The present invention relates to the field of vaccines, more specifically, to vaccines for intradermal delivery that simultaneously protect against various microorganisms. In particular, the invention relates to intradermal combination vaccines comprising *Mycoplasma* antigens and Porcine circovirus antigens, and their use for livestock immunization.

BACKGROUND ART

*Mycoplasma hyopneumoniae* and Porcine Circovirus type 2 (PCV2) are two of the most important pathogens affecting pigs causing significant economic losses in the swine industry.

*Mycoplasma* is a genus of bacteria that lack a cell wall around their cell membrane. Several species are pathogenic in swine, including *Mycoplasma hyopneumoniae* (*Mhyo*), which is known to cause porcine enzootic pneumonia, a highly contagious and chronic disease affecting pigs. As with other mollicutes, *M. hyopneumoniae* is small in size (400-1200 nm), has a small genome (893-920 kilo-base pairs) and lacks a cell wall.

Porcine enzootic pneumonia is an important cause of economic loss in the swine industry due to reduced weight gain and poor feed efficiency. In particular, this disease causes a chronic cough, dull hair coat, retarded growth and unthrifty appearance lasting several weeks. Characteristic lesions of purple to gray areas of consolidation, particularly in ventral apical and cardiac lobes, are observed in infected animals. Although the disease causes little mortality, affected swine are often prone to secondary infections by opportunistic pathogens, resulting in death or stress.

Treatment of *Mhyo* infection is limited to antibiotics, which are currently ineffective as they do not completely remove the infection. Vaccines have been found to reduce the severity of the disease but do not prevent the disease from occurring in infected pigs.

Another important pathogen for the livestock industry is Porcine circovirus. Porcine circoviruses (PCV) belong to the virus family Circoviridae and are small non-enveloped DNA viruses containing a unique single-stranded circular genome. The viral capsid is icosahedral and approximately 17 nm in diameter.

There are mainly two recognized genotypes of PCV: PCV type 1 (PCV1) and PCV type 2 (PCV2). PCV2 shares approximately 80% sequence identity with porcine circovirus type 1 (PCV1). However, in contrast with PCV1, which is generally non-virulent, infection of swine with PCV2 has been recently associated with a number of disease syndromes which have been collectively named Porcine Circovirus-Associated Diseases (PCVAD) (also known as Porcine Circovirus Diseases—PCVD). Postweaning Multisystemic Wasting Syndrome (PMWS) is generally regarded to be the major clinical manifestation of PCVAD. PMWS affects pigs between 5-18 weeks of age. PMWS is clinically characterized by wasting, paleness of the skin, unthriftiness, respiratory distress, diarrhea, icterus, and jaundice. In some affected swine, a combination of all symptoms will be apparent while other affected swine will only have one or two of these symptoms. During necropsy, microscopic and macroscopic lesions also appear on multiple tissues and organs, with lymphoid organs being the most common site for lesions. Mortality rates for swine infected with PCV2 can approach 80%. Currently, there are several vaccines in the market to protect swine from PCV2.

The majority of vaccines currently available for animal immunization against *Mhyo* or porcine circovirus are administered either subcutaneously (into the hypodermis) or intramuscularly (into the muscle). However, these routes of administration bypass the skin's immune system and deliver the antigens into fat or muscular tissue that have no important resident population of antigen-presenting cells. Antigen delivered to muscle tissue is thought to be picked up by transient antigen-presenting cells or simply to circulate to the draining lymph node.

Notwithstanding, in recent years an alternative route of vaccine administration has gained protagonism—the intradermal (ID) route. Intradermal vaccines deliver antigens directly into the dermis, an anatomical space that contains large numbers of antigen-presenting cells and thus, has the potential for greater immunogenicity than subcutaneous or intramuscular injection of a given amount of antigen. Hence, several advantages in terms of both immunogenicity (such as the ability to improve immune response in low-responders and the avoidance of the need for some adjuvants), and some practical issues (as the easier and safer administration with respect to conventional subcutaneous or intramuscular routes and the reduction in risk of needle-stick injuries for health care workers and blood vessels or nerves injuries for animals as it is usual to deliver ID vaccines by needle-less injectors) have prompted the use of ID route.

However, the type of vaccine (i.e. inactivated, attenuated, etc.) and its formulation (i.e. dose, adjuvants, etc.) might condition whether a particular vaccine can be administered intradermically or not. For instance, vaccines that contain aluminum-based or oil-in-water adjuvants are likely to have unacceptable local reactogenicity following intradermal administration.

As an example of ID vaccines, there are currently on the market vaccines for swine immunization against either *Mhyo* (Porcilis® *M Hyo* ID Once) or porcine circovirus (Porcilis® PCV ID). At present, no commercial bivalent ID vaccines containing PCV2 and *Mhyo* are available on the market.

In order to protect animals against these two common infections, workers have to perform two rounds of vaccination, duplicating the time and cost of the operation, and increasing the risks associated to vaccine and animal handling described above.

To solve the caveats derived from multiple vaccinations, it is usual in the immunization field to attempt to combine various antigens in a single vaccine. This is of particular importance when the pathogens against which protection is pursued are common pathogens of a particular animal species. However, the development of combination vaccines is not straightforward. The reduction in the immunogenicity of an antigen when combined with other components—as compared to the particular antigen administered alone—is known as interference. A further problem encountered in the formulation of combination vaccines is the inherent stability of their composite antigens over time. Vaccines in solution may undergo processes over time which decrease the immunogenicity of its antigen components, for instance the degradation of the antigen or the desorption of the antigens from the adjuvant to which they had been adsorbed. Another problem associated with combination vaccines is that they add an extra layer of complexity when a change in the route of administration or formulation, or a dose sparing strategy wants to be implemented, since the safety and activity of every antigen has to be maintained in the novel conditions.

An example of a combination vaccine is provided in WO2014009586, wherein it is disclosed the use of an intramuscular recombinant combination vaccine to protect animals against *Mycoplasma* and porcine circovirus infections. However, the formulation of the vaccine disclosed in said patent application is not suitable for intradermal injection due to its high volume and the reactogenic nature of its adjuvants. And as mentioned above, changing the formulation and/or route of administration is not straightforward, requiring extensive testing to determine the safety and efficacy.

More recently, the international application WO2017162741 disclosed an intradermal combination vaccine against *Mycoplasma* and porcine circovirus. However, in this document the authors show that only some specific combinations of adjuvant emulsions provide efficient and safe vaccines. Moreover, the experimental data presented in said document reveals that high concentrations of PCV2 antigens are needed in order to achieve immunization.

Although effective vaccines have been able to reduce the impact of *Mhyo* and PCV2, both pathogens continue to create challenges for hog producers worldwide. As previously mentioned, no commercial bivalent ID vaccines containing PCV2 and *Mhyo* are available on the market. Only bivalent vaccines for IM administration do exist, such as Porcilis® PCV *Mhyo* and Suvaxyn® Circo+MH RTU.

In view of the above, a need remains for expanding the repertoire of intradermal combination vaccines for swine protection that allow reducing the number of vaccine shots while protecting against several infectious diseases. The development of novel intradermal combination vaccines that enable multiple protection against different pathological conditions with simple and safe administrations procedures represents a step forward in the field of animal health.

SUMMARY OF INVENTION

The present inventors have discovered that a combination vaccine that combines *Mycoplasma hyopneumoniae* antigens and porcine circovirus antigens is capable of efficiently mounting an immune response that protects animals from the infection of both microorganisms, even when administered intradermally.

Importantly, the administration through the intradermal route is commonly carried out through needle-less injectors, which greatly facilitates vaccination procedure while reducing health risks to both animals and workers. Additionally, the vaccine of the invention presents the advantage that it contains antigens from both pathogens in a single working composition, which allows reducing the rounds of administration and the risk associated to them.

Thus, in a first aspect, the present invention provides a combination vaccine comprising one or more antigens of *Mycoplasma hyopneumoniae*, one or more antigens of porcine circovirus, and pharmaceutically acceptable excipients and/or carriers, for use in the prevention and/or treatment of porcine enzootic pneumonia and/or Porcine Circovirus-Associated Diseases (PCVAD) by administration of the vaccine into the dermis of livestock, wherein the one or more antigens of Porcine circovirus comprises the PCV2 ORF2 protein in an amount from 0.1 µg/dose to 10 µg/dose.

This aspect can also be formulated as the use of a combination vaccine comprising one or more antigens of *Mycoplasma hyopneumoniae* and one or more antigens of Porcine circovirus, wherein the one or more antigens of porcine circovirus comprises the PCV2 ORF2 protein in an amount from 0.1 µg/dose to 10 µg/dose, for the manufacture of a medicament for the prevention and/or treatment of porcine enzootic pneumonia and/or Porcine Circovirus-Associated Diseases (PCVAD) by administration of the medicament into the dermis of livestock. This embodiment can also be formulated as a method of intradermically immunizing livestock in need thereof with a combination vaccine comprising one or more antigens of *Mycoplasma hyopneumoniae* and one or more antigens of Porcine circovirus, wherein the one or more antigens of porcine circovirus comprises the PCV2 ORF2 protein in an amount from 0.1 µg/dose to 10 µg/dose, in particular for preventing and/or treating porcine enzootic pneumonia and/or Porcine Circovirus-Associated Diseases (PCVAD) by administration of the vaccine into the dermis of livestock.

Surprisingly, and as can be observed in Example 1, the inventors found out that the combination vaccine of the invention was efficient and safe even when the PCV2 antigen amount was greatly reduced (even below 1 µg per dose). Moreover, the combination vaccine was effective in a single dose. This was completely unexpected since combination vaccines commonly require higher antigen amounts than monovalent vaccines to counteract antigen interference—i.e. the reduction of antigen immunogenicity when combined with other antigens.

A second aspect of the invention provides an intradermal combination vaccine comprising one or more antigens of *Mycoplasma hyopneumoniae* and one or more antigens of porcine circovirus, wherein the one or more antigens of porcine circovirus comprises the porcine circovirus PCV2 ORF2 protein in an amount from 0.1 µg/dose to 10 µg/dose.

In a third and last aspect, the present invention provides a vaccination kit of parts comprising (a) an intradermal combination vaccine as defined in the second aspect of the invention, (b) optionally a delivery device suitable for intradermal delivery of vaccines; and (c) optionally, instructions for its use.

Figure 1:
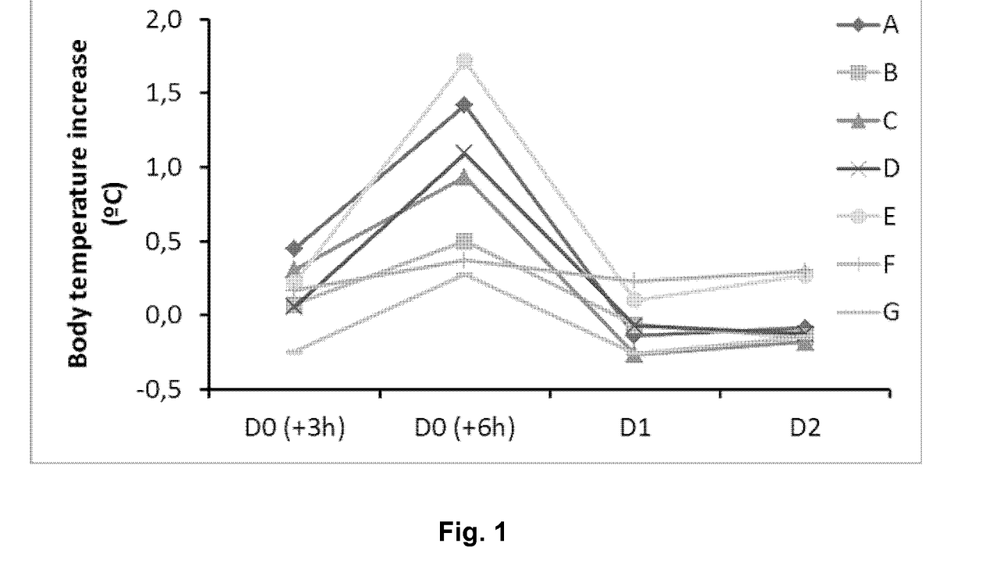
FIG. 1, related to Example 1, shows the body temperature of vaccinated piglets at different times after vaccination with the vaccine of the invention. D0 (+3 h) corresponds to three hours after vaccination; D0 (+6 h) corresponds to six hours after vaccination; D1, one day after vaccination; and D2, two days after vaccination. The groups of vaccinated piglets A to G are described in Example 1.
Figure 2:
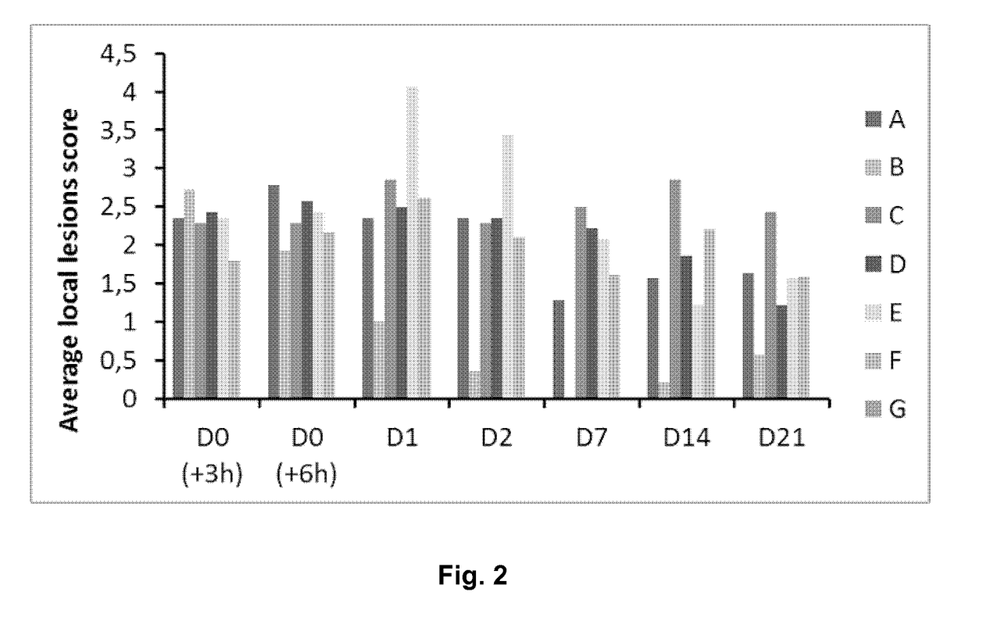
FIG. 2, related to Example 1, shows the local reactions score of piglets at various times after vaccination with the vaccine of the invention. D0 (+3 h) corresponds to three hours after vaccination; D0 (+6 h) corresponds to six hours after vaccination; D1, D2, D7, D14 and D21 correspond to one, two, seven, fourteen and twenty one days after vaccination, respectively. The groups of vaccinated piglets A to G are described in Example 1.

The inventors unexpectedly also discovered that using specific adjuvant formulations for the intradermal vaccine the efficiency of immunization was maintained while the safety was improved (see FIGS. 1 and 2).

Therefore, in a fourth aspect, the invention refers to an intradermal combination vaccine comprising one or more antigens of *Mycoplasma hyopneumoniae*, one or more antigens of Porcine circovirus, an adjuvant emulsion comprising mineral oil and an additive selected from a hydrophobic additive, an amphiphilic additive and combinations thereof, and pharmaceutically acceptable excipients and/or carriers.

In a fifth aspect, the invention provides the intradermal combination vaccine of the fourth aspect for use as a medicament in livestock.

In a sixth aspect, the invention provides a vaccination kit of parts comprising (a) an intradermal combination vaccine as defined in the fourth aspect; (b) optionally a delivery device suitable for intradermal delivery of vaccines; and (c) optionally, instructions for its use.

DETAILED DESCRIPTION OF THE INVENTION

Unless defined otherwise, all technical and scientific terms used herein have the same meaning as is commonly understood by one of skill in the art to which this invention belongs at the time of filling. However, in the event of any latent ambiguity, definitions provided herein take precedent over any dictionary or extrinsic definition. Further, unless otherwise required by context, singular terms shall include pluralities and plural terms shall include the singular.

The term "antigen" refers to a molecule against which a subject can initiate an immune response, e.g. a humoral and/or cellular immune response. Depending on the intended function of the composition, one or more antigens may be included.

The term "medicament" as used herein is synonymous of a pharmaceutical or veterinary drug (also referred to as medicine, medication, or simply drug) used to cure, treat or prevent disease in animals, including humans, as widely accepted. Drugs are classified in various ways. One key distinction is between traditional small-molecule drugs, usually derived from chemical synthesis, and biopharmaceuticals, which include recombinant proteins, vaccines, blood products used therapeutically (such as IVIG), gene therapy, monoclonal antibodies and cell therapy (for instance, stem-cell therapies). In the present invention medicament preferably is a veterinary medicament, and even more preferably is a vaccine for veterinary use.

The term "vaccine" as used herein, means an immunogenic composition accompanied by adequate excipients and/ or carriers, that when administered to an animal, elicits, or is able to elicit, directly or indirectly, an immune response in the animal. Particularly, the vaccines of the present invention elicit an immunological response in the host of a cellular or antibody-mediated type upon administration to the subject that it is protective. The term "intradermal vaccine" refers to vaccines administered into the dermis. The term "combination vaccine" means that the vaccine contains various antigens in a single preparation, protecting against two or more diseases or against one disease caused by two or more microorganisms. Thus, the vaccine includes as "active principle" an "immunogenic composition", which as used herein, refers to a material that elicits an immunological response in the host of a cellular or antibody-mediated immune response type to the composition upon administration to a vertebrate, including humans. The immunogenic composition comprises molecules with antigenic properties, such as killed or attenuated bacteria or virus, among others, and also immunogenic polypeptides. An immunogenic polypeptide is generally referred to as antigenic. A molecule is "antigenic" when it is capable of specifically interacting with an antigen recognition molecule of the immune system, such as an immunoglobulin (antibody) or T cell antigen receptor. An antigenic polypeptide contains an epitope of at least about five, and particularly at least about 10, at least 15, at least 20 or at least 50 amino acids. An antigenic portion of a polypeptide, also referred to as an epitope, can be that portion that is immunodominant for antibody or T cell receptor recognition, or it can be a portion used to generate an antibody to the molecule by conjugating the antigenic portion to a carrier polypeptide for immunization. The immunogenic composition relates according to this description, to the active molecule, composition comprising said molecule, or composition comprising more than one antigenic molecule to which a particular immune reaction is desired.

As for the expression "immunologically effective amount," or "immunologically effective dose" means the administration of that amount or dose of antigen, either in a single dose or as part of a series, that elicits, or is able to elicit, an immune response that reduces the incidence of or lessens the severity of infection or incident of disease in an animal for either the treatment or prevention of disease. The immunologically effective amount or effective dose is also able for inducing the production of antibody for either the treatment or prevention of disease. This amount will vary depending upon a variety of factors, including the physical condition of the subject, and can be readily determined by someone of skill in the art.

The term "inactivated cells" refers to cells that have been grown in culture and then killed by physical means (such as heat) or chemical means (such as contact with formaldehyde, BEI, or any other well-known inactivation agent) as the main ways of inactivation methods which the skilled man perfectly knows among others. The "inactivated cells" may be whole cells or partial cells, including cell lysates and supernatant recovered cells for example. The term "attenuated cells" refers to viable and replication competent cells the virulence of which has been reduced.

The term "livestock" relates to domesticated or farm animals raised to produce commodities such us food. Particularly, it relates to food-producing animals such as cattle, sheep, goats, swine, poultry (including egg-producing poultry), and equine animal. More in particular, it relates to food-producing animals such as cattle, sheep, goats, swine, poultry and equine animals. Even more in particular, in the present invention relates to swine species.

The term "carrier" is to be understood as a pharmaceutically acceptable component other than the immunogenic component. The carrier can be organic, inorganic, or both. Suitable carriers well known to those of skill in the art and include, without limitation, large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. In particular, it must be suitable for use in the intradermal route.

As used herein, the term "host" or "subject" is intended for the target individuals in need thereof to whom the immunogenic composition or vaccine of the invention are administered, among others humans, mammals, livestock, or any other animal species susceptible to be vaccinated with the compositions of the invention. Particularly, the mammal is from porcine species, more particularly is swine.

As used herein, the term "pig" or "swine" is intended for porcine species including, among others, pigs, boars, sows, gilts and piglets of any age or in any phase of their production cycle.

The term "preventing", "to prevent" or "prevention", include without limitation decreasing, reducing or ameliorating the risk of a symptom, clinical sings, disorder, condition, or disease, and protecting an animal from a symptom, clinical signs, disorder, condition, or disease. A prevention may be applied or administered prophylactically.

The term "treating", "to treat" or "treatment", include without limitation restraining, slowing, stopping, reducing, ameliorating, or reversing the progression or severity of an existing symptom, clinical sign, disorder, condition, or disease. A treatment may be applied or administered therapeutically.

The term "%w/w" or "percentage weight per weight" of a component refers to the amount of the single component relative to the total weight of the composition or, if specifically mentioned, of other component.

As used herein "mineral oil" refers to a variety of complex mixtures of hydrocarbons derived from inorganic matter, such as petroleum and/or liquid paraffin of different pharmaceutical grades. These mixtures are marketed under commercial names such as Marcol 52, Drakeol 5, Eolane 130, for example.

For "amphiphilic compound or additive" is to be understood a compound possessing both hydrophilic (water-affinity, polar) and lipophilic (fat-affinity) properties. Such a compound is called amphiphilic or amphipathic. Common amphiphilic substances are soaps, detergents and lipoproteins. Other examples of amphiphilic compounds are: Saponins, phospholipids, glycolipids, polysorbates. Amphiphilic compounds have lipophilic (typically hydrocarbon) structures and hydrophilic polar functional groups (either ionic or uncharged). In the particular case of block copolymers, the monomer units of one of the blocks have lipophilic structures meanwhile the monomer units of other blocks have polar functional groups. An example of amphiphilic block copolymer is poloxamer (block copolymer comprising units of polyethylene and polyoxypropylene). As a result of having both lipophilic and hydrophilic portions, some amphiphilic compounds may dissolve in water and to some extent in non-polar organic solvents. When placed in an immiscible biphasic system consisting of aqueous and organic solvents, the amphiphilic compound will partition the two phases. The extent of the hydrophobic and hydrophilic portions determines the extent of partitioning. For "hydrophobic additive or compound" is to be understood as a compound that deters water. In chemistry, it refers to the property of a substance to repel water. In actuality, it isn't that the substance is repelled by water so much as its lack of attraction to it. A hydrophobic substance exhibits hydrophobicity and may be termed a hydrophobe. Hydrophobic molecules tend to be nonpolar molecules that group together to form micelles rather than be exposed to water. Common hydrophobic substances are oils, cholesterol, lecithin, or polymer of isoprene units. An example of a hydrophobic polymer of isoprene units is squalene. As used herein, "hydrophobicity" can be tested, among others, using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;

ΔE is the energy of vaporization, cal/mole; and V is the molar volume, $cm^3$/mole. In an alternative way of definition, hydrophobic additives are those with a partition coefficient (P) logarithm (log P) greater than 0 (log P>0) (i.e. squalene has a log P=14.1 in a octanol/water). On the contrary, hydrophilic additives are those with a log P<0. A partition-coefficient (P) or distribution-coefficient (D) is the ratio of concentrations of a compound in a mixture of two immiscible phases at equilibrium. This ratio is therefore a measure of the difference in solubility of the compound in these two phases. The partition-coefficient generally refers to the concentration ratio of un-ionized species of compound whereas the distribution-coefficient refers to the concentration ratio of all species of the compound (ionized plus un-ionized). The skilled man in the art will know how to calculate this paremeter.

"Block copolymers" are polymers that comprise two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively. These di- and triblock-copolymers, can be sequential di- and triblock-copolymers or grafted di- and triblock-copolymers. Schematically a sequential diblock copolymer has the following structure—(A)n-(B)m-; a sequential triblock copolymer corresponds to the structure—(A)n-(B)m-(A)p-; a grafted copolymer is a segmented copolymer with a linear backbone of one composite and randomly distributed branches of another composite.

As described above, the present invention discloses an intradermal combination vaccine comprising one or more antigens of *Mycoplasma hyopneumoniae* and one or more antigens of PCV2 for use in the prevention and/or treatment of porcine enzootic pneumonia and/or Porcine Circovirus-Associated Diseases (PCVAD).

Different genotypes of PCV2 are encompassed in particular embodiments of the first aspect, such as PCV2a, PCV2b, PCV2c and PCV2d. There are currently five different PCV2 genotypes, designated as a-e. Genotypes of PCV2 are determined by the number of nucleotide substitutions in ORF 2 (capsid) divided by the total nucleotides in ORF2 (702 nt); this fraction is called p-distance. If the p-distance is greater than 0.035, the viruses are given a new genotype (Segalés J. et al., "PCV-2 genotype definition and nomenclature", Vet Rec., 2008; vol. 162(26), pp. 867-8). While this can be somewhat confusing, at least the nomenclature is standardized. The ORF2 of PCV2 encodes a protein of about 233 amino acids. Any PCV2 ORF2 is suitable to be used in the invention. PCV2 ORF2 sequences of different genotypes are disclosed in Segalés et al., 2008 or Xiao et al., "Global molecular genetic analysis of porcine circovirus type 2 (PCV2) sequences confirms the presence of four main PCV2 genotypes and reveals a rapid increase of PCV2d", J Gen Virol, 2015; vol. 96(Pt 7), pp.1830-41. Other new porcine circovirus such as PCV3 (disclosed in Palinski R. et al., "A Novel Porcine Circovirus Distantly Related to Known Circoviruses Is Associated with Porcine Dermatitis and Nephropathy Syndrome and Reproductive Failure", 2016, vol. 91(1)) are also encompassed in the invention.

The invention is meant to encompass all PCV2 ORF2 protein variants, for example the ones with the GenBank accession numbers AAC35310 (version AAC35310.1), AAC35331 (version AAC35331.1), or ABX71779 (version ABX71779.1), among others.

The one or more antigens of *Mycoplasma hyopneumoniae* and the one or more antigens of porcine circovirus in the intradermal combination vaccine are in an immunologically effective amount.

In a particular embodiment of the first aspect, optionally in combination with any embodiment above or below, the amount of the PCV2 ORF2 protein in the intradermal combination vaccine is from 0.1 µg/dose to 10 µg/dose. In a more particular embodiment, the amount of the PCV2 ORF2 protein is from 0.1 µg/dose to 5 µg/dose, and more preferably the amount of the PCV2 ORF2 proteins is from 0.5 µg/dose to 4 µg/dose.

As shown in the examples below, efficient immunization of livestock was achieved with the vaccine of the invention even when it contained amounts of PCV2 ORF2 protein as low as 0.6 µg/dose. This is surprising given that, as mentioned above, the combination vaccines commonly require higher amounts of antigens per dose to compensate for the antigen interference. The vaccine was efficacious even in a single-shot protocol, not requiring additional booster doses. Therefore, the two-dose protocol was not necessary.

Moreover, it supposes a real advantage in relation with the intradermal combination vaccines of the prior art against *Mycoplasma hyopneumoniae* and porcine circovirus (such as in WO2017162741), which contain high amounts of antigens.

With this particular combination, and as illustrated in examples, effective immunization of swine was achieved against antigens of both *Mycoplasma hyopneumoniae* and of porcine circovirus.

In a particular embodiment of the first aspect, optionally in combination with any embodiment above or below, the one or more antigens of *Mycoplasma hyopneumoniae* are in a form selected from the group consisting of isolated proteins of *Mycoplasma hyopneumoniae*, attenuated *Mycoplasma hyopneumoniae* cells, inactivated *Mycoplasma hyopneumoniae* cells, and combinations thereof. More particularly, the one or more antigens of *Mycoplasma hyopneumoniae* are in the form of inactivated *Mycoplasma hyopneumoniae* cells. Even more particularly, the one or more antigens of *Mycoplasma hyopneumoniae* are in the form of inactivated *Mycoplasma hyopneumoniae* cell lysates.

In a particular embodiment, optionally in combination with any embodiment above or below, the antigens in the intradermal combination vaccine of the first aspect are provided as inactivated *Mycoplasma hyopneumoniae* mutant strain cells, said mutant cells expressing one or more proteins of porcine circovirus. These *Mycoplasma hyopneumoniae* mutant strain cells comprise, in particular, one or more exogenous DNA sequence incorporated in the genome or in the cytosol thereof, said exogenous DNA sequence coding for at least one protein of porcine circovirus.

In another particular embodiment of the first aspect, optionally in combination with any embodiment above or below, the inactivated *Mycoplasma hyopneumoniae* cell of the combination vaccine of the invention is from a mutant strain of *Mhyo*, deposited by Laboratorios HIPRA, S.A. (and transferred to HIPRA Scientific S.L.U., the applicant) in Leibniz-Institut Deutsche Sammlung von Mikroorganismen and Zellkulturen (DSMZ) and selected from a mutant strain of *Mhyo* with the accession number DSM 26020; a mutant strain of *Mhyo* with the accession number DSM 26034; a mutant strain of *Mhyo* with the accession number DSM 26027; and a mutant strain of *Mhyo* with the accession number DSM 26033. All these mutant strains were deposited at DSMZ on May 29, 2012.

In another particular embodiment of the first aspect, optionally in combination with any embodiment above or below, the one or more *Mycoplasma hyopneumoniae* antigens are in the form of attenuated and/or inactivated *Mycoplasma hyopneumoniae* cells, in an amount from $10^3$ cells/dose to $10^{11}$ cells/dose. More particularly, from $10^5$ cells/dose to $10^{11}$ cells/dose, and more particularly from $10^9$ cells/dose to $10^{11}$ cells/dose.

In a more particular embodiment of the first aspect, optionally in combination with any embodiment above or below, the intradermal combination vaccine for use according to the first aspect is for use against another disease or pathological conditions affecting swine, the vaccine comprising one or more additional antigens selected from a microorganism which is selected from the group formed by *Actinobacillus* sp., *Brachyspira* sp., *Pasteurella multocida*, *Salmonella* sp., *Streptococcus* sp., *Isospora* sp., *Erysipelothrix rhusiopathiae*, *Leptospira* sp., *Staphylococcus* sp., *Haemophilus parasuis*, *Bordetella bronchiseptica*, *Clostridium* sp., *Mycoplasma* sp., *Lawsonia intracellularis*, *Escherichia coli*, porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, transmissible gastroenteritis coronavirus (TGEV), porcine epidemic diarrhea virus (PED) and torque teno virus (TTV).

Unexpectedly, the inventors also discovered that using a specific selection of adjuvants in the formulation of the intradermal combination vaccine for the use according to the first aspect, the efficacy was maintained while the safety was improved. In particular, the specified adjuvants diminished the rise in body temperature post-vaccination and reduced the severity of local reactions—as shown below in Example 1.

Therefore, in a more particular embodiment of the first aspect, optionally in combination with any embodiment above or below, the intradermal combination vaccine further comprises an adjuvant. In another embodiment, the adjuvant is an adjuvant emulsion comprising mineral oil and an additive, said additive selected from a hydrophobic additive, an amphiphilic additive and combinations thereof. In a more particular embodiment, the additive is selected from the group consisting of a polymer of isoprene units, a block copolymer, and combinations thereof. More particularly, the polymer of isoprene units is squalene and the block copolymer is a non-ionic block copolymer. More particularly, the non-ionic block copolymer is a poloxamer. Even more particularly, the poloxamer is of formula (I):

wherein a is an integer from 2 to 130 and b is an integer from 15-67. Even more particularly, a is 101 and b is 56.

In a more particular embodiment, optionally in combination with any embodiment above or below, the non-ionic block copolymer is Poloxamer 407 (Sigma), Pluronic F-127 (Acofarma), Kolliphor P407 (BASF), Poloxamer 188 such as Koliphor P188 (BASF), Poloxamer L121 such as Pluronic L121 (BASF). More particularly, the non-ionic block copolymer is Poloxamer 407 (Sigma). In particular, useful poloxamers are those with an hydrophilic-lipophilic balance (HLB) from 10 to 30, and more particularly from 18 to 24. HLB is a measure of the degree to which a compound is hydrophilic or lipophilic, determined standard procedures known by the skilled man.

Among other possible polymer of isoprene units to be used as additives in the adjuvant include hemiterpenes, monoterpenes, sesquiterpenes, diterpenes, sesterterpenes, other triterpenes different from squalene, and tetraterpenes.

This combination of adjuvants (mineral oil and additive) supposes a surprising effect, neither taught nor suggested from direct combination of monovalent antigenic ID vaccines against either Mhyo (Porcilis® M Hyo ID Once) or porcine circovirus (Porcilis® PCV ID). As above exposed, many are the factors conditioning if a particular vaccine can be administered intradermically or not, and the development of combination vaccines is not straightforward. Among the challenges to be overcome there is the reduction in the immunogenicity of an antigen when combined with other components. There are also the problems of inherent stability of their composite antigens over time; the degradation of the antigen, the maintenance of activity of every antigen in a dose sparing strategy and obtaining the adequate balance between safety and efficacy for all the antigens when combined and administered together.

In a particular embodiment of the first aspect, optionally in combination with any embodiment above or below, the intradermal combination vaccine further comprises an adjuvant emulsion comprising mineral oil and an additive selected from a hydrophobic additive, an amphiphilic additive and combinations thereof, wherein the concentration of mineral oil is from 5% w/w to 40% w/w and the concentration of the additive is from 0.5% w/w to 5% w/w. More particularly, the concentration of mineral oil is from 10% w/w to 25% w/w and the concentration of the additive is from 0.5% w/w to 2% w/w. More particularly, the concentration of mineral oil is 21.2% w/w and the concentration of the additive is 0.5% w/w. All percentages are relative to the total weight of the composition.

Yet in a more particular embodiment of the first aspect, the intradermal combination vaccine comprises mineral oil in a concentration from 5% w/w to 40% w/w and a non-ionic block copolymer in a concentration from 0.5% w/w to 5% w/w as additive in the adjuvant. Even in a more particular embodiment, the non-ionic block copolymer is the poloxamer of formula (I). More particularly, the poloxamer of formula (I) wherein a is 101 and b is 56.

In a more particular embodiment, optionally in combination with any embodiment above or below, the intradermal combination vaccine for use according to the first aspect further comprises a surfactant selected from the group consisting of alkylphenol ethoxylates, ethoxylated sorbitan esters, ethoxylated fatty alcohols, ethoxylated fatty acids, fatty acid alkanolamides, ethoxylated fatty acid alkanolamides, ethoxylated fatty amines, fatty amine oxides, fatty amidoamine oxides, fatty acid glycerides, sucrose esters, alkyl polyglycosides, ethylene oxide and propylene oxide copolymers, and ethoxylated and propoxylated fatty alcohols, and combinations thereof. More particularly, the surfactant is sorbitan monooleate.

In another particular embodiment, optionally in combination with any embodiment above or below, the intradermal combination vaccine further comprises an emulsifier selected from the group consisting of sorbitan Polysorbate 80, Montanox 80, Tween 80, Simulsol, Macrogol, and mixtures thereof. More particularly, the emulsifier is Polysorbate 80.

In another particular embodiment, the vaccine dose of an intradermal combination vaccine like the one of the invention is comprised from 0.05 to 0.5 ml, particularly from 0.1 to 0.2 ml.

The vaccine can be administered in one or more dose. A multiple-dose vaccination, as is well known in the art, consists of administering a first immunizing dose, followed by one or more additional doses which act as booster doses. In an embodiment of the invention, the vaccine preferably is of single-dose administration.

In a particular embodiment of the first aspect, optionally in combination with any embodiment above or below, the livestock is swine.

As detailed above, the present invention also provides an intradermal combination vaccine comprising one or more antigens of Mycoplasma hyopneumoniae and one or more antigens of porcine circovirus.

All particular embodiments of the intradermal combination vaccine for use according to the first aspect of the invention also apply to the intradermal combination vaccine of the second aspect of the invention.

In a particular embodiment of the second aspect, optionally in combination with any embodiment above or below, the one or more Mycoplasma hyopneumoniae antigens are in a form of attenuated and/or inactivated Mycoplasma hyopneumoniae cells, in an amount from $10^3$ cells/dose to $10^{11}$ cells/dose. More particularly, from $10^5$ cells/dose to $10^{11}$ cells/dose, and more particularly from $10^9$ cells/dose to $10^{11}$ cells/dose.

The one or more antigens of Mycoplasma hyopneumoniae and the one or more antigens of porcine circovirus in the combination vaccine of this second aspects are in immunologically effective amounts.

In another particular embodiment of the second aspect, optionally in combination with any embodiment above or below, the intradermal combination vaccine further comprises one or more additional antigens, wherein the additional antigen is selected from a group of microorganisms consisting of Actinobacillus, Bordetella, Borrelia, Brachyspira, Brucella, Campylobacter, Chlamydia and Chlamydophila, Clostridium, Corynebacterium, Enterococcus, Erysipelothrix, Escherichia, Francisella, Haemophilus, Helicobacter, Isospora, Lawsonia, Legionella, Leptospira, Listeria, Mycobacterium, Mycoplasma, Neisseria, Pasteurella, Pseudomonas, Rickettsia, Salmonella, Shigella, Staphylococcus, Streptococcus, Treponema Vibrio and Yersinia genus, and porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) and combinations thereof.

In another particular embodiment of the second aspect, optionally in combination with any embodiment above or below, the vaccine further comprises an adjuvant. In another embodiment, the adjuvant is an adjuvant emulsion comprising mineral oil and an additive selected from a hydrophobic additive, an amphiphilic additive and combinations thereof. In a more particular embodiment, the additive is selected from the group consisting of a polymer of isoprene units, block copolymers, and combinations thereof. More particularly, the polymer of isoprene units is squalene and the block copolymer is a non-ionic block copolymer. More particularly, the non-ionic block copolymer is a poloxamer. Even more particularly, the poloxamer is of formula (I):

wherein a is an integer from 2 to 130 and b is an integer from 15-67. Even more particularly, a is 101 and b is 56. In a more particular embodiment, the non-ionic block copolymer is Poloxamer 407 (Sigma), Pluronic F-127 (Acofarma), Kolliphor P407 (BASF), Poloxamer 188 such as Koliphor P188 (BASF), Poloxamer L121 such as Pluronic L121 (BASF). More particularly, is Poloxamer 407 (Sigma).

In a more particular embodiment of the second aspect, the intradermal combination vaccine comprises mineral oil in a concentration from 5% w/w to 40% w/w and a non-ionic block copolymer in a concentration from 0.5% w/w to 5% w/w as additive in the adjuvant. Even in a more particular embodiment, the non-ionic block copolymer is the poloxamer of formula (I). More particularly, the poloxamer of formula (I) wherein a is 101 and b is 56.

In a particular embodiment of the second aspect, optionally in combination with any embodiment above or below, the intradermal combination vaccine of the second aspect is for use as a medicament in livestock.

More in particular, the intradermal combination vaccine of the second aspect is for use in the prevention and/or treatment of porcine enzootic pneumonia and/or Porcine Circovirus-Associated Diseases (PCVAD) by administration of the vaccine into the dermis of livestock.

The invention also provides a vaccination kit comprising the vaccine of the second aspect of the invention. More particularly, the vaccination kit is for use in the prevention and/or treatment of a disease caused by Mycoplasma sp. and/or porcine circovirus. More particularly, for use in the prevention and/or treatment of porcine enzootic pneumonia caused by Mycoplasma and/or Porcine Circovirus-Associated Diseases (PCVAD).

As above disclosed, the invention also provides an intradermal vaccine comprising an adjuvant emulsion comprising mineral oil and an additive selected from a hydrophobic additive, an amphiphilic additive and combinations thereof.

In a particular embodiment of the fourth aspect, optionally in combination with any embodiment above or below, the additive of the intradermal combination vaccine is selected from the group consisting of a polymer of isoprene units, a block copolymer, and combinations thereof. More particularly, the polymer of isoprene units is squalene and the block copolymer is a non-ionic block copolymer. In a particular embodiment, the additive is a block copolymer. More particularly, the block copolymer is a non-ionic block copolymer. More particularly, the non-ionic block copolymer is a poloxamer. Even more particularly, the non-ionic block copolymer is a poloxamer of formula (I):

wherein a is an integer from 2 to 130 and b is an integer from 15-67. Even more particularly, the poloxamer a is 101 and b is 56. In a more particular embodiment, the non-ionic block copolymer is Poloxamer 407 (Sigma), Pluronic F-127 (Acofarma), Kolliphor P407 (BASF), Poloxamer 188 such as Koliphor P188 (BASF), Poloxamer L121 such as Pluronic L121 (BASF). More particularly, the non-ionic block copolymer is Poloxamer 407 (Sigma).

Among other possible polymer of isoprene units to be used as additives in the adjuvant include hemiterpenes, monoterpenes, sesquiterpenes, diterpenes, sesterterpenes, other triterpenes different from squalene, and tetraterpenes.

In a particular embodiment of the fourth aspect, optionally in combination with any embodiment above or below, the intradermal combination vaccine further comprises adjuvant emulsion, wherein the concentration of mineral oil is from 5% w/w to 40% w/w and the concentration of the additive is from 0.5% w/w to 5% w/w. More particularly, the concentration of mineral oil is from 10% w/w to 25% w/w and the concentration of the additive is from 0.5% w/w to 2% w/w. More particularly, the concentration of mineral oil is 21.2% w/w and the concentration of the additive is 0.5%w/w. All percentages relative to the total weight of the vaccine composition.

Yet in a more particular embodiment of this fourth aspect, the intradermal combination vaccine comprises mineral oil in a concentration from 5% w/w to 40% w/w and a non-ionic block copolymer in a concentration from 0.5% w/w to 5% w/w as additive in the adjuvant. Even in a more particular embodiment, the non-ionic block copolymer is the poloxamer of formula (I). More particularly, the poloxamer of formula (I) wherein a is 101 and b is 56.

In a particular embodiment of the fourth aspect, optionally in combination with any embodiment above or below, the one or more antigens of Mycoplasma hyopneumoniae in the intradermal combination vaccine are in a form selected from the group consisting of isolated proteins of Mycoplasma hyopneumoniae, for example and without limitation the P46, P65, P97, and P102 surface proteins, described in Minion et al., "The genome sequence of *Mycoplasma hyopneumoniae* strain 232, the agent of swine mycoplasmosis", J. Bacteriol., 2004, vol. 186(21), pp. 7123-7133; the P76, P146, P216 adhesins or the P95 membrane protein, described in Vasconcelos et al., "Swine and poultry pathogens: the complete genome sequences of two strains of *Mycoplasma hyopneumoniae* and a strain of *Mycoplasma synoviae*", J. Bacteriol., 2005, vol. 187(16), pp. 5568-5577, or the P36 cytosolic protein described in Caron et al., "Diagnosis and differentiation of *Mycoplasma hyopneumoniae* and *Mycoplasma hyorhinis* infections in pigs by PCR amplification of the p36 and p46 genes", J. Clin. Microbiol., 2000, vol. 38(4), pp. 1390-1396, or ribosomal RNA, attenuated *Mycoplasma hyopneumoniae* cells, inactivated *Mycoplasma hyopneumoniae* cells, and combinations thereof. More particularly, the one or more antigens of *Mycoplasma hyopneumoniae* are in the form of inactivated *Mycoplasma hyopneumoniae* cells. Even more particularly, the one or more antigens of *Mycoplasma hyopneumoniae* are in the form of inactivated *Mycoplasma hyopneumoniae* cell lysates.

In a particular embodiment of the fourth aspect, optionally in combination with any embodiment above or below, the one or more antigens of porcine circovirus are in a form selected from the group consisting of inactivated porcine circovirus particles, attenuated porcine circovirus particles, isolated proteins of porcine circovirus, and combinations thereof. More particularly, the one or more antigens of porcine circovirus are isolated proteins of porcine circovirus. Even more particularly, the one or more antigens are selected from the group comprising ORF1, ORF2, and ORF3 proteins. More particularly, the antigen is ORF2 protein.

In another embodiment, optionally in combination with any embodiment above or below, the porcine circovirus is a porcine circovirus type 2 (PCV2).

Different genotypes of PCV2 are encompassed in particular embodiments of the first aspect, such as PCV2a, PCV2b, PCV2c and PCV2d. There are currently five different PCV2 genotypes, designated as a-e. Genotypes of PCV2 are determined by the number of nucleotide substitutions in ORF 2 (capsid) divided by the total nucleotides in ORF2 (702 nt); this fraction is called p-distance. If the p-distance is greater than 0.035, the viruses are given a new genotype (Segalés et al., 2008). While this can be somewhat confusing, at least the nomenclature is standardized. The ORF2 of PCV2 encodes a protein of about 233 amino acids. Any PCV2 ORF2 is suitable to be used in the invention. PCV2 ORF2 sequences of different genotypes are disclosed in Segalés et al., 2008 or Xiao et al., 2015. Other new porcine circovirus such as PCV3 (disclosed in Palinski R. et al., 2016) are also encompassed in the invention.

The invention is meant to encompas all PCV2 ORF2 protein variants, for example the ones with the GenBank accession numbers AAC35310 (version AAC35310.1), AAC35331 (version AAC35331.1), or ABX71779 (version ABX71779.1), among others.

In a particular embodiment of the fourth aspect, optionally in combination with any embodiment above or below, the antigens of the intradermal combination vaccine are inactivated *Mycoplasma hyopneumoniae* mutant strain cells, said cells expressing one or more protein of porcine circovirus.

In another particular embodiment of the fourth aspect, optionally in combination with any embodiment above or below, the inactivated *Mycoplasma hyopneumoniae* (*Mhyo*) cell is from a mutant strain of *Mhyo* deposited in Leibniz-Institut DSMZ and selected from a mutant strain of *Mhyo* with the accession number DSM 26020; a mutant strain of *Mhyo* with the accession number DSM 26034; a mutant strain of *Mhyo* with the accession number DSM 26027; and a mutant strain of *Mhyo* with the accession number DSM 26033.

The one or more antigens of *Mycoplasma hyopneumoniae* and the one or more antigens of porcine circovirus in the intradermal combination vaccine of this fourth aspect are in immunologically effective amounts. In a particular embodiment, the amount of porcine circovirus antigens is from 0.1 µg/dose to 10 µg/dose, more particularly from 0.1 µg/dose to 5 µg/dose, even more particularly from 0.5 µg/dose to 4 µg/dose. In another particular embodiment, the amount of antigens of *Mycoplasma hyopneumoniae* in the combination vaccine is from $10^3$ cells/dose to $10^{11}$ cells/dose. More particularly, from $10^5$ cells/dose to $10^{11}$ cells/dose, and more particularly from $10^9$ cells/dose to $10^{11}$ cells/dose.

In another particular embodiment, the vaccine dose of an intradermal combination vaccine like the one of the invention is comprised from 0.05 to 0.5 ml, particularly from 0.1 to 0.2 ml.

In another particular embodiment of the fourth aspect, optionally in combination with any embodiment above or below, the intradermal combination vaccine further comprises one or more additional antigens wherein the additional antigen is selected from a group of microorganisms consisting of *Actinobacillus*, *Bordetella*, *Borrelia*, *Brachyspira*, *Brucella*, *Campylobacter*, *Chlamydia* and *Chlamydophila*, *Clostridium*, *Corynebacterium*, *Enterococcus*, *Erysipelothrix*, *Escherichia*, *Francisella*, *Haemophilus*, *Helicobacter*, *Isospora*, *Lawsonia*, *Legionella*, *Leptospira*, *Listeria*, *Mycobacterium*, *Mycoplasma*, *Neisseria*, *Pasteurella*, *Pseudomonas*, *Rickettsia*, *Salmonella*, *Shigella*, *Staphylococcus*, *Streptococcus*, *Treponema Vibrio* and *Yersinia* genus, and porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) and combinations thereof.

As disclosed above, the invention also provides an intradermal combination vaccine for use as a medicament in livestock.

In a particular embodiment of the fifth aspect, optionally in combination with any embodiment above or below, the vaccine is for use in the prevention and/or treatment of porcine enzootic pneumonia caused by *Mycoplasma hyopmeumoniae* and/or Porcine Circovirus-Associated Diseases (PCVAD) in livestock. This embodiment can also be formulated as the use of the intradermal combination vaccine of the fifth aspect of the invention for the manufacture of a medicament for the prevention and/or treatment of porcine enzootic pneumonia and/or Porcine Circovirus-Associated Diseases (PCVAD) by administration of the medicament into the dermis of livestock. This embodiment can also be formulated as a method for intradermically immunizing livestock in need thereof with the combination vaccine of the fifth aspect, in particular for the prevention and/or treatment of porcine enzootic pneumonia caused by *Mycoplasma* and/or Porcine Circovirus-Associated Diseases (PCVAD).

In a particular embodiment of the fifth aspect, optionally in combination with any embodiment above or below, the livestock is swine.

In a particular embodiment of the fifth aspect, the vaccine is for use in the prevention and/or treatment of an additional disease, wherein the vaccine comprises one or more additional antigens selected from a microorganism selected from the group formed by *Actinobacillus* sp., *Brachyspira* sp., *Pasteurella multocida*, *Salmonella* sp., *Streptococcus* sp., *Isospora* sp., *Erysipelothrix rhusiopathiae*, *Leptospira* sp., *Staphylococcus* sp., *Haemophilus parasuis*, *Bordetella bronchiseptica*, *Clostridium* sp., *Mycoplasma* sp., *Lawsonia intracellularis*, *Escherichia coli*, porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, transmissible gastroenteritis coronavirus (TGEV), porcine epidemic diarrhea virus (PED) and torque teno virus (TTV).

As described above, the invention also refers to a vaccination kit of parts comprising (a) an intradermal combination vaccine of the fourth aspect; (b) optionally a delivery device suitable for intradermal delivery of vaccines; and (c) optionally, instructions for its use.

In a particular embodiment of the sixth aspect, optionally in combination with any embodiment above or below, the vaccination kit is for use in the prevention and/or treatment of a disease caused by *Mycoplasma* sp. and/or porcine circovirus. More particularly, for use in the prevention and/or treatment of porcine enzootic pneumonia caused by *Mycoplasma* and/or Porcine Circovirus-Associated Diseases (PCVAD).

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

Particular clauses of the invention are as follows:

Clause 1. An intradermal combination vaccine comprising:
one or more antigens of *Mycoplasma hyopneumoniae*;
one or more antigens of porcine circovirus;
an adjuvant emulsion comprising mineral oil and an additive selected from a hydrophobic additive, an amphiphilic additive and combinations thereof; and
pharmaceutically acceptable excipients and/or carriers.

Clause 2. The intradermal combination vaccine according to clause 1, wherein the additive is selected from the group consisting of a polymer of isoprene units, a block copolymer, and combinations thereof.

Clause 3. The intradermal combination vaccine according to clause 2, wherein the additive is a block copolymer.

Clause 4. The intradermal combination vaccine according to clause 3, wherein the block copolymer is a non-ionic block copolymer.

Clause 5. The intradermal combination vaccine according to clause 4, wherein the non-ionic block copolymer is a poloxamer.

Clause 6. The intradermal combination vaccine according to clause 5, wherein the poloxamer is of formula (I):

$$HO\left[\diagdown\diagup O\right]_a\left[\diagdown\underset{CH_3}{\diagup}O\right]_b\left[\diagdown\diagup O\right]_a H \quad (I)$$

wherein a is an integer from 2 to 130 and b is an integer from 15-67;

Clause 7. The intradermal combination vaccine according to clause 6, wherein in the poloxamer a is 101 and b is 56.

Clause 8. The intradermal combination vaccine according to any of clauses 1-7, wherein the one or more antigens of *Mycoplasma hyopneumoniae* are in a form selected from the group consisting of isolated proteins of *Mycoplasma hyopneumoniae*, attenuated *Mycoplasma hyopneumoniae* cells, inactivated *Mycoplasma hyopneumoniae* cells, and combinations thereof.

Clause 9. The intradermal combination vaccine according to clause 8, wherein the one or more antigens of *Mycoplasma hyopneumoniae* are in the form of inactivated *Mycoplasma hyopneumoniae* cells.

Clause 10. The intradermal combination vaccine according to any of clauses 1-9, wherein the one or more antigens of porcine circovirus are in a form selected from the group consisting of inactivated porcine circovirus particles, attenuated porcine circovirus particles, isolated proteins of porcine circovirus, and combinations thereof.

Clause 11. The intradermal combination vaccine according to any of clauses 1-10, wherein the one or more antigens of porcine circovirus are in the form of isolated proteins of porcine circovirus.

Clause 12. The intradermal combination vaccine according to any of clauses 1-11, wherein the antigens are inactivated *Mycoplasma hyopneumoniae* mutant strain cells, said cells expressing one or more proteins of porcine circovirus.

Clause 13. The intradermal combination vaccine according to clause 12, wherein the inactivated *Mycoplasma hyopneumoniae* cell is from a mutant strain of *Mhyo* deposited in Leibniz-Institut DSMZ and selected from a mutant strain of *Mhyo* with the accession number DSM 26020; a mutant strain of *Mhyo* with the accession number DSM 26034; a mutant strain of *Mhyo* with the accession number DSM 26027; and a mutant strain of *Mhyo* with the accession number DSM 26033.

Clause 14. The intradermal combination vaccine according to any of the previous clauses, further comprising one or more additional antigens wherein the additional antigen is selected from a group of microorganisms consisting of *Actinobacillus*, *Bordetella*, *Borrelia*, *Brachyspira*, *Brucella*, *Campylobacter*, *Chlamydia* and *Chlamydophila*, *Clostridium*, *Corynebacterium*, *Enterococcus*, *Erysipelothrix*, *Escherichia*, *Francisella*, *Haemophilus*, *Helicobacter*, *Isospora*, *Lawsonia*, *Legionella*, *Leptospira*, *Listeria*, *Mycobacterium*, *Mycoplasma*, *Neisseria*, *Pasteurella*, *Pseudomonas*, *Rickettsia*, *Salmonella*, *Shigella*, *Staphylococcus*, *Streptococcus*, *Treponema Vibrio* and *Yersinia* genus, and porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) and combinations thereof.

Clause 15. An intradermal combination vaccine as defined in any of clauses 1-14, for use as a medicament in livestock.

Clause 16. The intradermal combination vaccine for use according to clause 15, which is for use in the prevention and/or treatment of porcine enzootic pneumonia caused by *Mycoplasma hyopneumoniae* and/or Porcine Circovirus-Associated Diseases (PCVAD), and optionally against another disease or pathological conditions affecting swine.

Clause 17. The intradermal combination vaccine for use according to any of clauses 15-16, wherein the livestock is swine.

Clause 18. The intradermal combination vaccine for use according to any of clauses 15-17, which is for use in the prevention and/or treatment of an additional disease, the vaccine comprising one or more additional antigens selected from a microorganism selected from the group formed by *Actinobacillus* sp., *Brachyspira* sp., *Pasteurella multocida*, *Salmonella* sp., *Streptococcus* sp., *Isospora* sp., *Erysipelothrix rhusiopathiae*, *Leptospira* sp., *Staphylococcus* sp., *Haemophilus parasuis*, *Bordetella bronchiseptica*, *Clostridium* sp., *Mycoplasma* sp., *Lawsonia intracellularis*, *Escherichia coli*, porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, transmissible gastroenteritis coronavirus (TGEV), porcine epidemic diarrhea virus (PED) and torque teno virus (TTV).

Clause 19. A vaccination kit of parts comprising:
(a) an intradermal combination vaccine as defined in any of clauses 1-14;
(b) optionally a delivery device suitable for intradermal delivery of vaccines; and
(c) optionally, instructions for its use.

Clause 20. The vaccination kit of parts as defined in clause 19 for use in the prevention and/or treatment of a disease caused by *Mycoplasma* sp. and/or porcine circovirus.

EXAMPLES

Example 1

Safety and Efficacy of Different Intradermal Combined Vaccines Against Porcine Circovirus Associated Disease (PCVAD) and Enzootic Pneumonia: at Fixed PCV2 ORF2 Concentration per Dose.

The objective of this study was to assess the safety and efficacy of different combined *M. hyopneumoniae* and PCV2 intradermal vaccine formulations against enzootic pneumonia (EP) and porcine circovirus associated disease (PCVAD) in piglets. The study was carried out under a randomised and fully blinded basis.

A total of 47 piglets of 6 weeks old, free of antibodies against *M. hyopneumoniae*, were selected for the study. The animals had high maternally derived antibodies against PCV2. The piglets were allotted to 6 treatment groups (Group A to G) of 7 piglets each, except for group F in which 5 piglets were included.

All piglets were vaccinated at day 0 of study by intradermal route with a single dose of 0.2 ml of the corresponding formulae applied with a needle-free device (such as the one disclosed in WO2016102619, HIPRA SCIENTIFIC, S.L.U., Spain). The combined vaccines of the group A to E contained the same antigenic material, 0.6 µg/dose of PCV2 ORF2 protein and $1.57\times10^{10}$ *M. hyopneumoniae* inactivated cells/dose. Group F received a single dose of 0.2 ml of the commercial available vaccine PORCILIS® MHYO ID ONCE (monovalent vaccine containing *M.hyo* antigen only) applied with the IDAL vaccinator (MSD Animal Health) and a single dose of 2 ml of the commercial available vaccine PORCILIS® PCV (monovalent vaccine containing PCV2 ORF2 antigen only) given simultaneously by intramuscular route with a needle-syringe system. Finally, Group G received a 0.2 ml of placebo (PBS) by intradermal route in the same way as Groups A to E.

Different adjuvants were also tested for each group:
Group A: *M.hyo*/PCV2 combined vaccine containing 21.2% of mineral oil.
Group B: *M.hyo*/PCV2 combined vaccine containing 21.2% mineral oil and 2% of block copolymer (Poloxamer 407, BASF).
Group C: *M.hyo*/PCV2 combined vaccine containing 30% mineral oil and 5% of squalene.
Group D: *M.hyo*/PCV2 combined vaccine containing 21.2% mineral oil and 5% of squalene.
Group E: *M.hyo*/PCV2 combined vaccine containing Montanide IMS 251 (SEPPIC).
Group F: PORCILIS® MHYO ID ONCE and PORCILIS® PCV (*M.hyo* monovalent ID vaccine and PCV2 ORF2 monovalent IM vaccine, respectively; MSD Animal Health), both containing mineral oil and dl-α-tocopheryl acetate as adjuvants according to their respective EU Marketing Authorisation, Summary of Product Characteristics.
Group G: placebo, injected with PBS.

On study day 29 all piglets were challenged with virulent PCV2b and virulent *M. hyopneumoniae*. 3 ml/piglet (1.5 ml for each nostril) of PCV2b virulent strain was inoculated intranasally. For the *M. hyopneumoniae* infection, intratracheal route was used and 10 ml/piglet of a virulent *M. hyopneumoniae* strain were inoculated.

Safety

All piglets were observed daily for clinical signs. The main variable for safety evaluation was body temperature and local and systemic reactions to vaccination.

Body temperatures were observed and recorded for each piglet at the day of vaccination (before vaccination, and 3 and 6 hours post-vaccination) and until day 2 post-vaccination. Local reactions of the vaccines were observed at day 0 (at 3 and 6 hours after vaccination) and at days 1, 2, 7, 14 and 21 days post-vaccination. These reactions were assessed by the average of local reactions score. The score was calculated based on the size, colour and appearance of lesion (if any) at the point of vaccination.

Results are summarized in FIGS. 1 and 2.

Body temperature increase reached its maximum peak 6 hours post-vaccination in all groups. One day post-vaccination body temperature returned to basal values. The higher mean peak value was at D0 (+6 h postvaccination) for Group E which contained IMS 251 (SEPPIC) with an increase up to 1.7° C. (41.7° C.) whereas values in the control group were in the 39-40° C. range. The mean body temperature increase in the vaccinated groups A, C, D, containing different mineral oil concentrations (21.2%, 30%+squalene and 21.2%+squalene, respectively) was between 0.9 -1.5° C.

Group B (21.2% mineral oil +Poloxamer 407) recorded a temperature increase of only 0.5° C. very similar with the values obtained with control group G and group F (vaccinated with the monovalent Porcilis® MHYO ID ONCE and Porcilis® PCV, simultaneously). It was demonstrated that the group that received the vaccine adjuvanted with 2% of Poloxamer 407 plus mineral oil reduced the body temperature of an equivalent combination protocol of the vaccines without this component.

Regarding local reactions assessed by visual inspection and palpation, no animals in the control groups had any local reactions. The Montanide IMS 251 (Group E) registered superior local reactions score up to 2 days post-vaccination when compared to the other group formulations. The study also revealed that the higher mineral oil concentration in the combined vaccine the longest local reactions recorded. Group F, Porcilis MHYO ID ONCE, had higher local reactions that lasted up to days 14 and 21 post-vaccination when compared to Group B. The best local safety was achieved in Group B, which contained mineral oil at 21.2% supplemented with Poloxamer 407.

Efficacy

Blood samples were collected from all animals on the days 21 and 1 before vaccination and as well on Day 14, 21, 31, 45, 53 and 56 post-vaccination. Samples were tested for antibodies against PCV2 and Mhyo. Efficacy of Mhyo was assessed by surface of affected with M.hyopneumoniae-like lesions in the different treatment groups.

M. hyopneuminae Efficacy

The main variable for challenge efficacy evaluation was the pulmonary lesion scoring. Each lung lobe was scored between 0 and 5 according to the proportion of affected tissue with M. hyopneumoniae-like lesions (i.e. lung consolidation):

TABLE 1

| Score | Percentage of affected lung |
|---|---|
| 0 | 0% |
| 1 | 0-20% |
| 2 | 20-40% |
| 3 | 40-60% |
| 4 | 60-80% |
| 5 | 80-100% |

In order to obtain a weighted score ranging between 0 and 5 that takes into account the contribution of each lung lobe to the total lung weight, the following formula was applied:

$$(RA \times 0.11) + (LA \times 0.05) + (RC \times 0.1)(LC \times 0.06) + (RD \times 0.34) + (LD \times 0.29) + (I \times 0.05) = \text{Weighted Score}$$

Then, the percentage of affected lung was calculated using the weighted score value.

Figure 3:
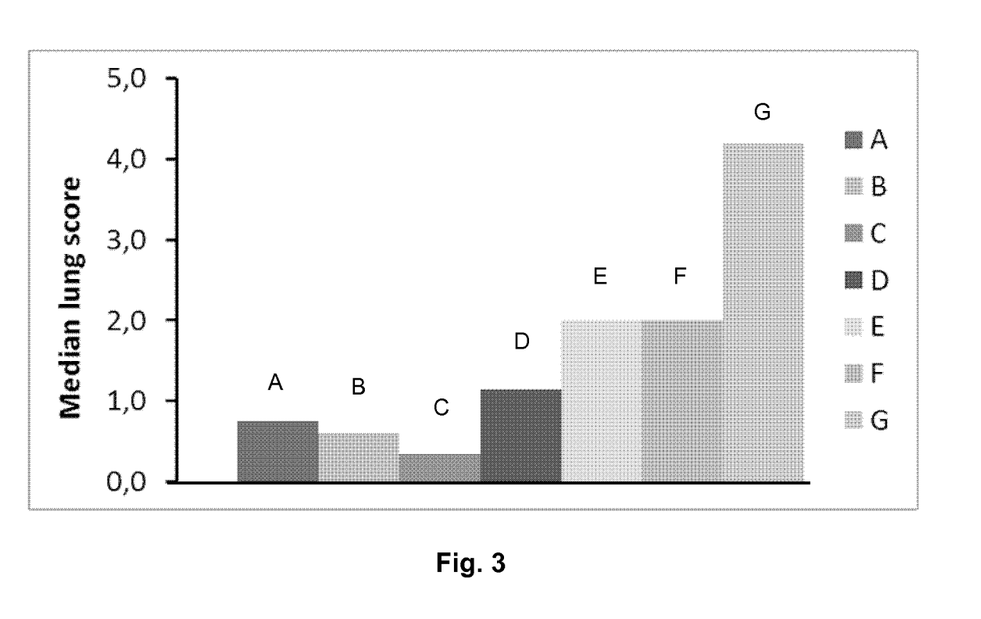
FIG. 3, related to Example 1, shows the pulmonary lesion score of vaccinated pigs at day 27 after the challenge infection with *Mycoplasma hyopneumoniae*. The groups of vaccinated piglets A to G are described in Example 1.
Figure 4:
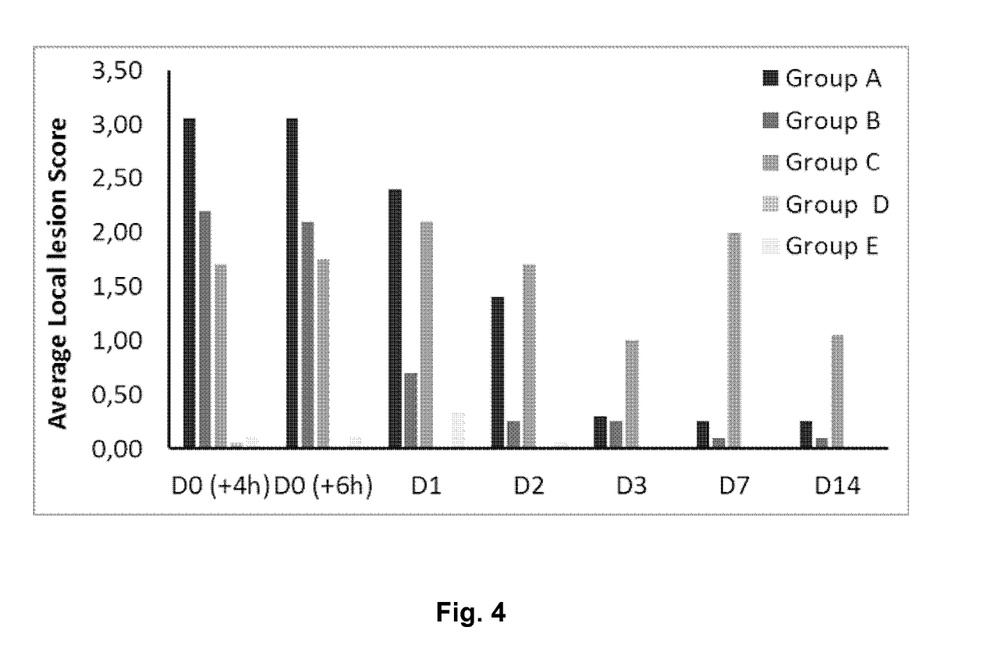
FIG. 4, related to Example 2, shows the local reactions score of piglets at various times after vaccination with the vaccine of the invention. D0 (+3 h) corresponds to three hours after vaccination; D0 (+6 h) corresponds to six hours after vaccination; D1, D2, D7, D14 and D21 correspond to one, two, seven, fourteen and twenty one days after vaccination, respectively. The groups of vaccinated piglets A to E are described in Example 2.
Figure 5:
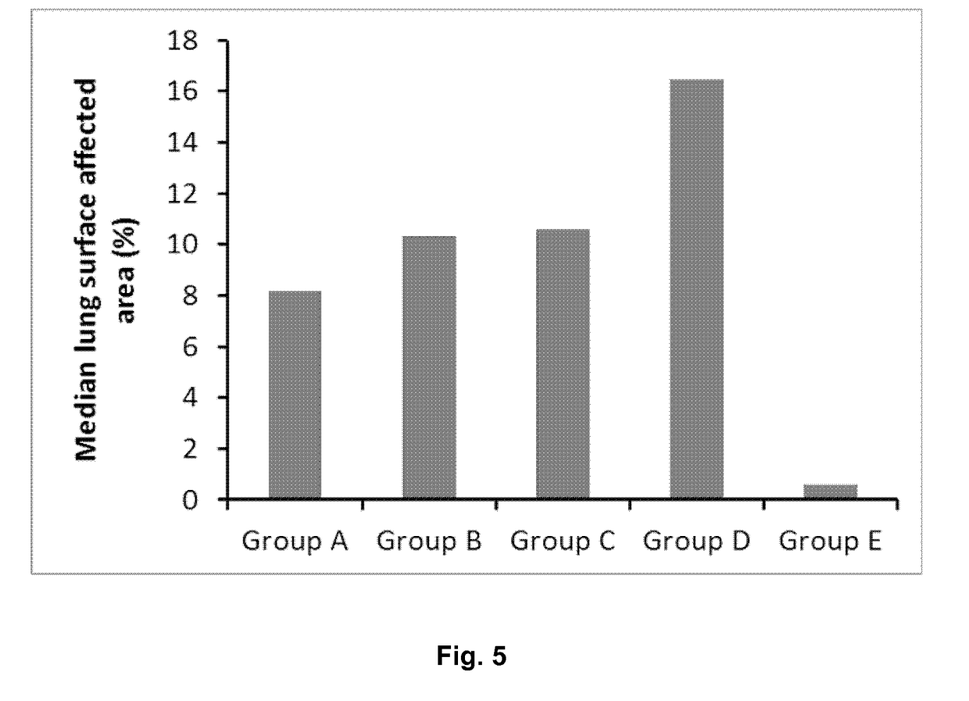
FIG. 5, related to Example 2, shows the percentage of median lung surface affected area of vaccinated pigs at day 28 after the challenge infection with *Mycoplasma hyopneumoniae*. The groups of vaccinated piglets A to E are described in Example 2.

At day 27 after infection (D56) all animals were humanely euthanized. During necropsy animals were analyzed for M. hyopneumoniae lung lesions. All the vaccinated groups had lower lesion scores than the control PBS group.

The study revealed that Montanide IMS 251 (Group E) and Porcilis® MHYO ID ONCE +Porcilis® PCV (Group F) had the highest lung lesion scores, whereas Groups A to D based on formulations containing mineral oil alone or in combination with other components such as squalene and poloxamer 407 performed better with less lung lesion scores. Although Group C containing the higher mineral oil concentration (30%) gave better results in terms of efficacy against a Mhyo challenge, Group B vaccinated with the formulae containing 21.2% of mineral oil and 2% of block copolymer (Poloxamer 407) performed better in both safety and efficacy.

PCV2 Efficacy

Seroconversion to PCV2 was observed after challenge in all groups except for the non-vaccinated challenged (Group G).

Therefore, it is demonstrated that these M.hyo/PCV2 intradermal combined vaccines (formulations administered to groups A to E) achieve an effective response to PCV2 challenge even when containing low amounts of ORF2 PCV2 capsid protein per dose.

Example 2

Safety and Efficacy of Intradermal One-shot Combined Vaccines Against Porcine Circovirus Associated Disease (PCVAD) and Enzootic Pneumonia: at Different PCV2 ORF2 Concentration/Dose.

The objective of this study was to assess the safety and efficacy of different combined M.hyopneumoniae and PCV2 intradermal vaccines when formulated with different concentrations of PCV2 ORF2 protein per dose and also with different concentrations of mineral oil against enzootic pneumonia (EP) and porcine circovirus associated disease (PCVAD) in piglets.

The study was carried out under a randomised and fully blinded basis.

A total of 50 piglets, either male or female, of 4 weeks of age free of antibodies against M.hyopneumoniae and with low levels of maternal derived antibodies against PCV2 were used in this study. The piglets were allotted to 4 treatment groups of 10 animals each (A to D), Group E acted as a sentinel group. Each group received a different vaccination treatment at day 0 of the study.

1. Group A: vaccinated intradermally with a single dose of 0.2 ml of a combined vaccine comprising $3 \times 10^{10}$ inactivated M. hyopneumoniae cells and 1.25 µg of PCV2 ORF2 protein per dose, adjuvanted with 21.2% mineral oil and 0.5% of a block copolymer.
2. Group B: vaccinated intradermally with a single dose of with 0.2 ml of a vaccine comprising $2.2 \times 10^{10}$ inactivated M. hyopneumoniae cells and 1.49 µg of PCV2 ORF2 protein per dose, containing as adjuvant 15% of mineral oil and 0.5% of block copolymer.
3. Group C: the piglets were co-administered of two commercially available vaccines. The piglets received 0.2 ml of the vaccine PORCILIS® MHYO ID ONCE (MSD Animal Health) administered intradermally, and 2 ml of PORCILIS® PCV2 (MSD Animal Health) given intramuscularly in the opposite side of the neck.
4. Group D: this group received 2 ml of PBS intramuscularly, as non-vaccinated challenged group.
5. Group E: this group received 0.2 ml of PBS intradermally, as non-vaccinated non-challenged group.

A co-infection model of PCV2 and M. hyopneumoniae was used to evaluate the vaccines efficacy. The experimental challenge was carried out by intranasal infection four weeks after vaccination for groups A, B, C and D. Group E was not infected and served as non-vaccinated non-challenged control. The piglets received an inoculum of (i) 3 ml of virulent PCV2b strain inoculated intranasally by cannula to each animal (1.5 ml to each nostril), and (ii) 5 ml/piglet of virulent M.hyopneumoniae strain inoculated by cannula (2.5 ml to each nostril). The *M.hyopneumoniae* challenge was repeated for 3 consecutive days.

At day 28 after challenge (study day 56) pigs were humanely euthanized. In order to assess the efficacy of the combined vaccines. *M. hyopneumoniae* lung lesions were scored. Tonsil, inguinal, mesenteric and mediastinal lymph nodes were collected for PCV2 quantification by Q-PCR. Furthermore, local and systemic reactions were evaluated during the study.

Results

Safety

Before vaccination, piglets were observed for general health. Body temperatures were recorded for all piglets on day 0 before vaccination, at 4 and 6 hours after vaccination, and on days 1, 2 and 3 post-vaccination. Local reactions were also recorded at day 0 (at 4 and 6 hours after vaccination), and on days 1, 2, 3, 7 and 14 post-vaccination. The mean temperature increase was calculated for each group. All vaccinated groups had a slight increase in the average body temperature at 6 hours post vaccination. The maximum temperature increase was 1.03°C. in Group A, which is acceptable for swine vaccines.

All vaccinated groups showed animals with local reactions. However, group A and B containing mineral oil plus block copolymer adjuvant performed better. While an initial local reaction score peak at the day of vaccination and day 1 post-vaccination was observed in both groups A and B, the local reactions were rapidly reduced after 3 days post-vaccination. In contrast, the group C (vaccinated with Porcilis® *MHYO* ID ONCE and Porcilis® PCV) had important local lesions associated to the ID route that persisted until day 14 (last day that local lesions were monitored).

Based on the results it may be concluded that the combined *Mhyo* and PCV2 intradermal vaccines A and B resulted in good safety profile. Regarding to local reactions it may be also concluded that the combined *Mhyo* and PCV2 intradermal A and B vaccines are even safer than when vaccinating with commercially available monovalent vaccines, as the monovalent Porcilis® *MHYO* ID ONCE vaccine led to important local reactions until day 14 in comparison to the bivalent intradermal A and B vaccines, in which local lesions were seen to be reduced at day 2 post vaccination.

Furthermore, one out of ten piglets in group C vaccinated intramuscularly with Porcilis® PCV2 showed an anaphylactic reaction, while none of the twenty piglets vaccinated with an intradermal vaccine (Groups A and B) showed any systemic reaction. It may be concluded that intradermal vaccination, wherever the formula, was safer than the intramuscular vaccine in terms of systemic reactions.

*M. hyopneumoniae* Efficacy

The main variable for challenge efficacy evaluation was the pulmonary lesion scoring. The score was calculated as described in Example 1.

At the end of the study all animals were humanely euthanized. During necropsy animals were analyzed for *M. hyopneumoniae* lung lesions.

The results of *M. hyopneumoniae* lung lesions showed that the combined bivalent intradermal vaccines A and B clearly reduced the percentage of lung affected compared to the negative control group (FIG. 2). It is also shown that when using the bivalent *Mhyo* and PCV2 vaccines A and B, a greater reduction of the lung lesion area was observed.

PCV2 Efficacy.

The main variable for efficacy evaluation was the reduction of PCV2 viremia determined by Q-PCR. Seroconversion to PCV2, proportion of PCR positive animals, and clinical signs were also evaluated.

Figure 6:
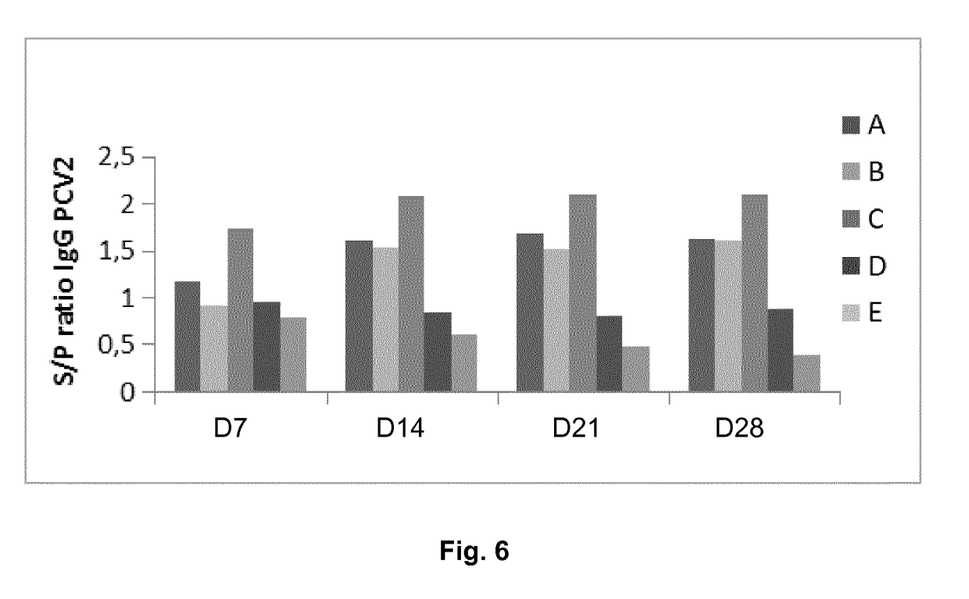
FIG. 6, related to Example 2, shows the seroconversion to PCV2 ORF2 (S/P ratio) of vaccinated pigs at days 7 (D7), 14 (D14), 21 (D21), and 28 (D28) after the PCV2 challenge. The groups of vaccinated piglets A to E are as described in Example 2.

PCV2 IgG antibodies in sera were analysed at days 7, 14, 21 and 28 post-infection using Porcine Circovirus type 2 Antibody Test Kit (BioChek). S/P ratios were calculated (FIG. 6). The results demonstrate the efficacy of all vaccines, as all vaccinated groups increased significantly the seroconversion when compared to control groups.

Q-PCR was performed on sera and nasal swabs at days 7, 14, 21 and 28 post-infection (days of study 35, 42, 49, 56). PCV2 genomic DNA in each sample was quantified by PCR. At the end of the study all animals were necropsied and PCV2 titer in different tissues such as lung, tonsil, mediastinal, mesenteric, and inguinal lymph nodes were analyzed.

The results demonstrated that the percentage of animals positive to PCV2 by Q-PCR was reduced in the vaccinated groups when compared to the negative control group.

There were significant differences between all the vaccinated groups and negative control in the reduction of PCV2 titers in different tissues. These results also demonstrated that the *M.hyo*/PCV2 combined A and B vaccine was efficacious against PCV2.

In conclusion, intradermal *M.hyo*/PCV2 combined vaccines containing mineral oil and block copolymer, led to safe profile, even safer than commercial monovalent available ID vaccine. At the same time, the new *M.hyo*/PCV2 combined A and B vaccines also gave an efficacious response against PCV2 and *M. hyopneumoniae*.

The study also demonstrated that these *M.hyo*/PCV2 intradermal combined vaccines (Groups A and B) achieve effective PCV2 response even when containing low amounts of ORF2 PCV2 capsid protein per dose.

CITATION LIST

WO2014009586
WO2016102619
WO2017162741

Segalés J. et al., "PCV-2 genotype definition and nomenclature", Vet Rec., 2008; vol. 162(26), pp. 867-8.

Minion et al., "The genome sequence of *Mycoplasma hyopneumoniae* strain 232, the agent of swine mycoplasmosis", J. Bacteriol., 2004, vol. 186(21), pp. 7123-7133.

Vasconcelos et al., "Swine and poultry pathogens: the complete genome sequences of two strains of *Mycoplasma hyopneumoniae* and a strain of *Mycoplasma synoviae*", J. Bacteriol., 2005, vol. 187(16), pp. 5568-5577.

Caron et al., "Diagnosis and differentiation of *Mycoplasma hyopneumoniae* and *Mycoplasma hyorhinis* infections in pigs by PCR amplification of the p36 and p46 genes", J. Clin. Microbiol., 2000, vol. 38(4), pp. 1390-1396

Palinski R. et al., "A Novel Porcine Circovirus Distantly Related to Known Circoviruses Is Associated with Porcine Dermatitis and Nephropathy Syndrome and Reproductive Failure", 2016, vol. 91(1).

Xiao et al., "Global molecular genetic analysis of porcine circovirus type 2 (PCV2) sequences confirms the presence of four main PCV2 genotypes and reveals a rapid increase of PCV2d", J Gen Virol, 2015; vol. 96(Pt 7), pp.1830-41.

The invention claimed is:

1. A method for the prevention and/or treatment of porcine enzootic pneumonia and/or Porcine Circovirus-Associated Diseases (PCVAD) comprising administering into the dermis of livestock in need thereof a single-dose combination vaccine comprising one or more antigens of *Mycoplasma hyopneumoniae*, one or more antigens of porcine circovirus, an adjuvant and pharmaceutically acceptable excipients and/or carriers, wherein the one or more antigens of porcine circovirus comprises the PCV2 ORF2 protein in an amount from 0.1 μg/dose to 10 μg/dose.

2. The method according to claim 1, wherein the amount of the PCV2 ORF2 protein is from 0.5 μg/dose to 4 μg/dose.

3. The method according to claim 1, wherein the one or more antigens of *Mycoplasma hyopneumoniae* are in a form selected from the group consisting of isolated proteins of *Mycoplasma hyopneumoniae*, attenuated *Mycoplasma hyopneumoniae* cells, inactivated *Mycoplasma hyopneumoniae* cells, and combinations thereof.

4. The method according to claim 1, wherein the one or more antigens of *Mycoplasma hyopneumoniae* are in a form of inactivated *Mycoplasma hyopneumoniae* cells, in an amount from $10^3$ cells/dose to $10^{11}$ cells/dose.

5. The method according to claim 1, which additionally is for the prevention and/or treatment of another disease or pathological conditions affecting swine, wherein the vaccine comprises one or more additional antigens selected from a microorganism which is selected from the group formed by *Actinobacillus* sp., *Brachyspira* sp., *Pasteurella multocida*, *Salmonella* sp., *Streptococcus* sp., *Isospora* sp., *Erysipelothrix rhusiopathiae*, *Leptospira* sp., *Staphylococcus* sp., *Haemophilus parasuis*, *Bordetella bronchiseptica*, *Clostridium* sp., *Mycoplasma* sp., *Lawsonia intracellularis*, *Escherichia coli*, porcine reproductive and respiratory syndrome virus (PRRS), swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, transmissible gastroenteritis coronavirus (TGEV), porcine epidemic diarrhea virus (PED) and torque teno virus (TTV).

6. The method according to claim 1, wherein the adjuvant is an adjuvant emulsion comprising mineral oil and an additive selected from a hydrophobic additive, an amphiphilic additive and combinations thereof.

7. The method according to claim 6, wherein the additive is selected from the group consisting of a polymer of isoprene units, a block copolymer, and combinations thereof.

8. The method according to claim 7, wherein the additive is a non-ionic block copolymer of formula (I):

wherein a is an integer from 2 to 130 and b is an integer from 15-67.

9. The method according to claim 8, wherein a is 101 and b is 56.

10. The method according to claim 1, wherein the livestock is swine.

11. An intradermal single-dose combination vaccine comprising one or more antigens of *Mycoplasma hyopneumoniae* and one or more antigens of porcine circovirus, wherein the one or more antigens of porcine circovirus comprises the porcine circovirus PCV2 ORF2 protein in an amount from 0.1 μg/dose to 10 μg/dose, and an adjuvant.

12. The intradermal single-dose combination vaccine according to claim 11, wherein the one or more antigens of *Mycoplasma hyopneumoniae* are in the form of attenuated and/or inactivated *Mycoplasma hyopneumoniae* cells, in an amount from $10^3$ cells/dose to $10^{11}$ cells/dose.

13. The intradermal single-dose combination vaccine according to claim 11, further comprising one or more additional antigens wherein the additional antigen is selected from a group of microorganisms consisting of *Actinobacillus*, *Bordetella*, *Borrelia*, *Brachyspira*, *Brucella*, *Campylobacter*, *Chlamydia* and *Chlamydophila*, *Clostridium*, *Corynebacterium*, *Enterococcus*, *Erysipelothrix*, *Escherichia*, *Francisella*, *Haemophilus*, *Helicobacter*, *Isospora*, *Lawsonia*, *Legionella*, *Leptospira*, *Listeria*, *Mycobacterium*, *Mycoplasma*, *Neisseria*, *Pasteurella*, *Pseudomonas*, *Rickettsia*, *Salmonella*, *Shigella*, *Staphylococcus*, *Streptococcus*, *Treponema Vibrio* and *Yersinia* genus, and porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) and combinations thereof.

14. The intradermal single-dose combination vaccine according to claim 11, wherein the adjuvant is and adjuvant emulsion comprising mineral oil and an additive selected from a hydrophobic additive, an amphiphilic additive and combinations thereof.

15. The intradermal single-dose combination vaccine according to claim 14, wherein the additive is selected from the amphiphilic non-ionic block copolymer of formula (I):

wherein a is an integer from 2 to 130 and b is an integer from 15-67.

16. The intradermal single-dose combination vaccine according to claim 15, wherein a is 101 and b is 56.

17. A vaccination kit of parts comprising:
(a) a single-dose intradermal combination vaccine as defined in claim 11;
(b) optionally a delivery device suitable for intradermal delivery of vaccines; and
(c) optionally, instructions for its use.

* * * * *